United States Patent [19]

Aaby et al.

[11] 4,344,440

[45] Aug. 17, 1982

[54] MICROPROBE FOR MONITORING BIOPHYSICAL PHENOMENA ASSOCIATED WITH CARDIAC AND NEURAL ACTIVITY

[76] Inventors: Trygve Aaby, 312 S. Hayford St., Lansing, Mich. 48910; Barnett Rosenberg, 2687 Ramparte Path, Holt, Mich. 48824

[21] Appl. No.: 136,317

[22] Filed: Apr. 1, 1980

[51] Int. Cl.³ .............................................. A61B 5/04
[52] U.S. Cl. .................................. 128/653; 324/58 B; 324/58.5 B; 343/772
[58] Field of Search ............... 128/653, 718, 715, 748, 128/804; 179/1 ST; 324/58 B, 58.5 B; 343/772; 329/161, 193

[56] References Cited

U.S. PATENT DOCUMENTS

| | | | |
|---|---|---|---|
| 2,407,690 | 9/1946 | Southworth | 128/804 |
| 3,102,232 | 8/1963 | Leonard et al. | 324/58.5 B |
| 3,115,131 | 12/1963 | Holliday | 128/653 |
| 3,483,860 | 12/1969 | Namerow | 128/653 |
| 3,561,430 | 2/1971 | Filler et al. | 128/661 |
| 3,796,208 | 3/1974 | Bloice | 128/653 |
| 3,951,134 | 4/1976 | Malech | 128/653 |
| 4,085,740 | 4/1978 | Allen, Jr. | 128/653 |
| 4,138,998 | 2/1979 | Nowogrodzki | 128/736 |
| 4,162,500 | 7/1979 | Jacobi et al. | 128/653 |

OTHER PUBLICATIONS

Pedersen, P. C. et al, "An Investigation of Microwave Radiation for Pulmonary Diagnostics", IEEE BME Transactions, vol. BM23, No. 5, pp. 410-412, Sep. 1976.
Robinson, J. E. et al, "Microwave Heating of Malignant Mouse Tumors and Tissue Equivalent Phantom Systems", Jrnl. Microwave Power, vol. 11, No. pp. 87-98, Jun. 1976.
Susskind, C. "Possible Use of Microwaves in Management of Lung Disease", Proc. IEEE, vol. 61, pp. 673-674, (May 1973).
Susskind, C. et al, "Oscillograph Field Plotter", Electronics, vol. 24, p. 140, Sep. 1951.
Pedersen, P. C. et al, "Microwave Reflection & Transmission Measurements for Pulmonary Diagnoses & Monitoring", IEEE BME Trans., vol. 25, pp. 40-48, Jan. 1978.
Bragg, D. G. et al, "Monitoring & Diagnosis of Pulmonary Edema by Microwaves: A Preliminary Report", Invest. Radiology, vol. 12, pp. 289-291, May-Jun. 1977.
Griffin, D. W., "MW Interferometers for Biol. Studies", Microwave Jrnl., vol. 21, pp. 69-72, May 1978.
Schwan, H. P., "Microwave Biophysics", Microwave Power Engrg., E. C. O'Kress ed., (Academic Press 1978), pp. 213-214.
Salati, O. M. et al, "RF Radiation Hazards", Electronic Industries, pp. 96-101, (Nov. 1962).
Yamaura, J., "Mapping of Microwave Power Transmitted Through the Human Thorax", Proc. of IEEE, vol. 67, pp. 1170-1171, (Aug. 1978).
Lin, J. C. et al, "Microwave Apexcardiography", IEEE Trans. on Microwave Theory & Tech., vol. MTT-27, pp. 618-620, (Jun. 1979).

*Primary Examiner*—Kyle L. Howell
*Assistant Examiner*—Francis J. Jaworski
*Attorney, Agent, or Firm*—Kerkam, Stowell, Kondracki & Clarke

[57] ABSTRACT

A portable microprobe uses 10 gigahertz CW microwave radiation at a power level of less than 10 milliwatts for recording of a number of biophysical phenomena associated with the cardiac and neural activity of the life system. The microprobe consists of a Gunn diode feeding power into a short, insulated dielectric waveguide, the free end of which houses a point contact semiconductor diode isolated by a metal shield from the incident beam. The wave guide concentrates and delivers a pencil shaped beam into the tissue of interest and the back-scattered radiation is modulated and detected by the diode. The detected signal is filtered, amplified and recorded to reflect on-going biological activity. The receiver electronics is housed in a small self-contained package and has its output connected through a flexible attachment to two ear tubes which enable continuous monitoring of the audio response through an electrical and audio converter indicative of the on-going biological activity. By scanning step wise across the chest, the microprobe allows localization of many details of cardiac activity. The microprobe can also be used to monitor activities of the brain and the spinal cord.

28 Claims, 14 Drawing Figures

1 SEC

FIG. 14.

MICROPROBE FOR MONITORING BIOPHYSICAL PHENOMENA ASSOCIATED WITH CARDIAC AND NEURAL ACTIVITY

BACKGROUND OF THE INVENTION

1. Field of the Invention

The present invention relates to the use of back-scattered microwave radiation for non-invasive monitoring and diagnostics of biological activity, physiologic activity, anatomical structure and the pathology of various organs of living animals and man.

2. Description of the Prior Art

The use of microwaves in monitoring biological activity and pathological diagnostics is receiving more and more attention, particularly because microwaves are capable of penetration of soft tissue and can be used in non-invasive techniques for monitoring the heart, brain and other organs. Two examples of such techniques are disclosed in U.S. Pat. Nos. 3,483,860 to Namarow and 3,951,314 to Malech.

U.S. Pat. No. 3,483,860 to Namarow discloses a method for monitoring intrasomatic circulatory functions and organ movement wherein low power microwave signals are modulated with an audio frequency and transmitted through a horn antenna positioned on a subject's chest. A portion of such signals is reflected back and received through a directional coupler. The received signals are modulated in accordance with heart action, i.e. variations in blood flow during the pumping cycle and movement of the heart and adjacent bodily organs. The modulated signals are amplified and demodulated in a receiver, the modulation envelope being impressed on the audio carrier frequency. While providing an important diagnostic tool, because of the use of a horn antenna large areas are irradiated and it is not possible to isolate for diagnosis small localized areas. Also, since the system depends on variations in blood flow or muscle or heart movement, it cannot be used for medical diagnosis of areas such as the brain which is free from movement or the spine which is substantially transparent to microwaves.

U.S. Pat. No. 3,951,134 to Malech discloses a method and apparatus for remotely monitoring brain waves. Electromagnetic signals of different frequencies are simultaneously transmitted to the brain of the subject. It is suggested that the signals of different frequencies penetrate the subject's skull and mix to form an interference waveform which is modulated by brain activity. The modulated interference waveform is re-transmitted from the brain and picked up by the antenna and processed in received electronics to develop a signal representing intra-brain activity. While the Malech patent provides a means of monitoring brain function which may be a useful barometer of organic functions, it is too technically cumbersome to be accepted as a general diagnostic tool by the general practioner.

Over the years researchers have reported various techniques for using microwaves as a means for biological studies and reference may be made to the following publications.

(1) C. Susskind, "Possible Use of Microwaves in the Management of Lung Disease," *Proc. IEE,* Vol. 61, pp. 673-74 (May 1973);

(2) C. Susskind and A. R. Perrins, "Oscillograph Field Plotter," *Electronics,* Vol. 24, pg. 140 (September 1951);

(3) P. C. Pedersen et al., "An Investigation of the Use of Microwave Radiation for Pulmonary Diagnostics," *IEEE Transactions on Biomedical Engineering,* Vol. BME-22, pp. 410-12 (September 1976);

(4) P. C. Pedersen et al., "Microwave Reflection and Transmission Measurements for Pulmonary Diagnosis and Monitoring," *IEEE Transactions on Biomedical Engineering,* Vol. BME-25, pp. 40-48 (January 1978);

(5) D. G. Bragg et al., "Monitoring and Diagnosis of Pulmonary Edema by Microwaves: A Preliminary Report," *Investigative Radiology,* Vol. 12, pp. 289-91 (May-June 1977);

(6) D. W. Griffin, "MW Interferometers for Biological Studies," *Microwave Journal,* Vol. 21, pp. 69-72 (May 1978);

(7) H. P. Schwan, "Microwave Biophysics," *Microwave Power Engineering,* E. C. O'Kresss, ed. (Academic Press. 1968) pp. 213-34;

(8) O. M. Salati et al., "Radio Frequency Radiation Hazards," *Electronic Industries,* pp. 96-101 (November 1962);

(9) J. Yamaura, "Mapping of Microwave Power Transmitted Through the Human Thorax," *Proceedings of the IEEE,* Vol. 67, pp. 1170-71 (August 1978; and (10) J. C. Lin et al., "Microwave Apexcardiography," *IEEE Transactions on Microwave Theory and Techniques,* Vol. MT-27, pp. 618-20 (June 1979).

While much research has been funded to develop microwave techniques for diagnostic testing and large amounts of funds have been spent in the development of sophisticated laboratory electronics to support such research, little attention has been paid toward the development of diagnostic instruments or tools capable of every day use by the general practioner. Perhaps one reason for the absence of interest in this area is the traditional reluctance of medical practioners in deviating from accepted practice and the use of tools or instruments radically different from those which have served the profession well over the years.

SUMMARY OF THE INVENTION

It is a primary object of the present invention to provide a microwave diagnostic instrument for probing and monitoring on-going biological activity, physiologic activity, anatomical structure and the pathology of various organs of living animals and man.

Another object of the present invention is to provide a portable microwave diagnostic instrument which can operate at safe levels of radiation and which can be used for monitoring heart and other organ activity and to study activities of the brain and spinal cord.

A further object of the present invention is to provide a portable microwave diagnostic instrument that may be used as a substitute for a stethoscope by converting localized heart activity into monaural or binaural sounds.

Still another object of the present invention is to provide a portable diagnostic instrument capable of monitoring electrical activity of the brain and spinal cord.

Accordingly, the present invention relates to a method and apparatus for directing and concentrating a low power level microwave signal on localized body areas such as the heart and other organs, spine and brain to non-invasively monitor on-going biological or neural activity. A Gunn diode feeds power into one end of a short, insulated dielectric wave guide, the free end of which houses a point contact semiconductor isolated by a metal shield from the incident beam. The wave guide concentrates and directs a pencil shaped beam through the free end onto a small localized area. Back scattered radiation is detected, filtered, amplified and recorded to reflect on-going biological or neural activity. The microwave instrumentation is housed to form a compact portable unit capable of being carried by a physician much the same way as a stethoscope and includes two ear tubes connected to receive the audio output of the amplifier through an audio converter to provide a monaural or binaural signal indicative of the on-going biological or neural activity.

A BRIEF DESCRIPTION OF THE DRAWINGS

Other objects and advantages of the invention will be further apparent from the following description and the accompanying drawings which form part of the instant specification and which are to be read in conjunction therewith, and in which like reference numerals are used to identify like parts throughout the several views.

In the drawings.

DESCRIPTION OF THE PREFERRED EMBODIMENTS

Figures 1, 2:
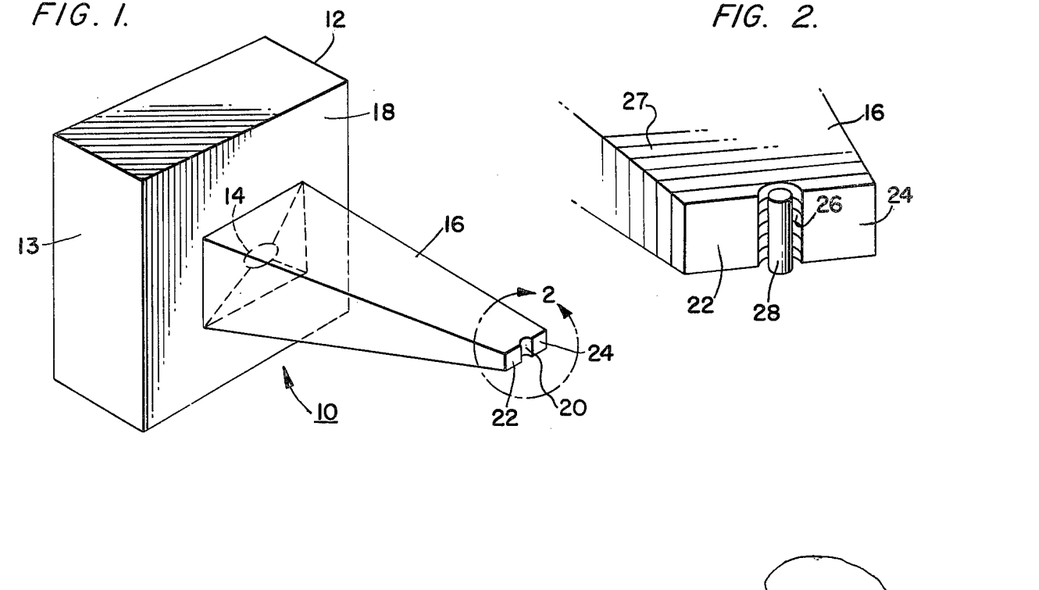
FIG. 1 is a perspective view of a "microprobe" in accordance with the present invention.
FIG. 2 is a enlarged, fragmentary view of the free end of the waveguide shown in FIG. 1 within the dash line circle.

Referring now to FIG. 1, there is shown the "heart" of the microwave monitoring system of the present invention which for convenience will be referred to as the "microprobe" 10. Microprobe 10 comprises a conventional miniature self-contained Gunn diode 12 and associated resonating chamber 13 formed by planar walls and having an output window 14 in one wall. Diode 12 is powered by a suitable DC voltage supply not shown in FIG. 1. The DC supply may be a well known type such as Thornton model MWG-103, or batteries.

Gunn diode 12 has its output window 14 coupled to one end of a tapered dielectric waveguide 16 mounted to wall 18 of resonating chamber 13. Guide 16 has a decreasing or reducing taper in the direction of its output end. As shown in FIG. 1, waveguide 16 is truncated to form a frustum of a solid regular trapezoid and has a small groove 20 cut into the free end of the waveguide forming microwave exit ports 22 and 24 to each side of the groove. Groove 20 is lined with a metallic shield 26 which may be of aluminum or copper as shown more clearly in FIG. 2 and a detector diode 28 is mounted within the groove which together with the reflector serves as a housing for the small diode detector. Negligible power due to field fringing is received at the detector unless an object is placed in front of the waveguide to produce backscattering of radiation. The outer planar surfaces of waveguide 16 may also be provided with a metallic shield 27 of aluminum foil or copper foil. Other metal layers such as gold or silver may also be utilized. Such a shield is not essential for operation of the microprobe; however, the shield improves microwave response and cancels stray fields.

Waveguide 16 is preferably a solid dielectric such as plexiglass; however, any suitable plastic transparent to microwaves may be used. The material selected should be such that the impedance at the exit ports 22-24 approximates the impedance of the subject to be monitored, i.e. the surface against which the microprobe is pressed. To this end, the impedance of the waveguide may be modified by incorporating into the plastic suitable fillers such as titanium dioxide to change the dielectric constant of the solid material forming the waveguide. While waveguide 16 is shown as having flat tapering sides forming a solid regular trapezoid, other shapes will readily suggest themselves. For example, waveguide 16 may take the form of a truncated cone. It is, however, important that the dielectric waveguide 16 tapers to a gradually reduced cross section at the output end such that the microwave power output signal from the Gunn diode 12 is polarized and focused into a beam as it passes through the inside of the dielectric guide. The cross sectional area of the output end of the guide at exit ports 22 and 24 should be approximately 1 square centimeter. The high refractive index of the dielectric serves to shorten the effective wavelength and allows propagation of the beam through the exit ports 22 and 24 at the end of the waveguide in the order of 1 square centimeter or less. Thus, there is provided a highly localized beam which enables diagnostic measurements to be made of discreet areas of organs. The localization can be further restricted by increasing the frequency of the microwave source. In the preferred embodiment, the diode provides a continuous frequency output of 10 gigahertz. However, by varying the diode and resonating chamber, the output frequency of the emitted signal can be changed over a wide range of, say, 5 gigahertz to 20 gigahertz.

The continuous wave output radiation has a total power output level of less than 10 milliwatts. Thus, monitoring of biophysical activity of a life system can be accomplished safely with a minimum of hazard to the life system. The penetration depth, defined as the distance to attentuate the beam power to 1/e of the incident level for a 10 gigahertz wave is 0.34 cm. in high water content tissue and 3.0 cm. in fat or boney tissue. The wavelength in these two types of tissue are 0.46 cm. and 1.41 cm. respectively.

Many geometries are possible for detecting scattered microwave radiation at all angles from 0° to 180°. The microprobe 10 may be scanned slowly across the area of the life system or subject being monitored and evaluated or several detectors may be arranged in an array. It is also possible to detect backscattered waves by physically separating the detector 28 from the microprobe 10. This advantageously enables one to obtain spatial distribution of the scattered waves. However, in the preferred embodiment the detector diode 28 is disposed at the center of the exit end of the waveguide, centrally disposed between ports 22 and 24. This arrangement provides a better signal to noise ratio and minimizes power level requirements.

Figure 3:
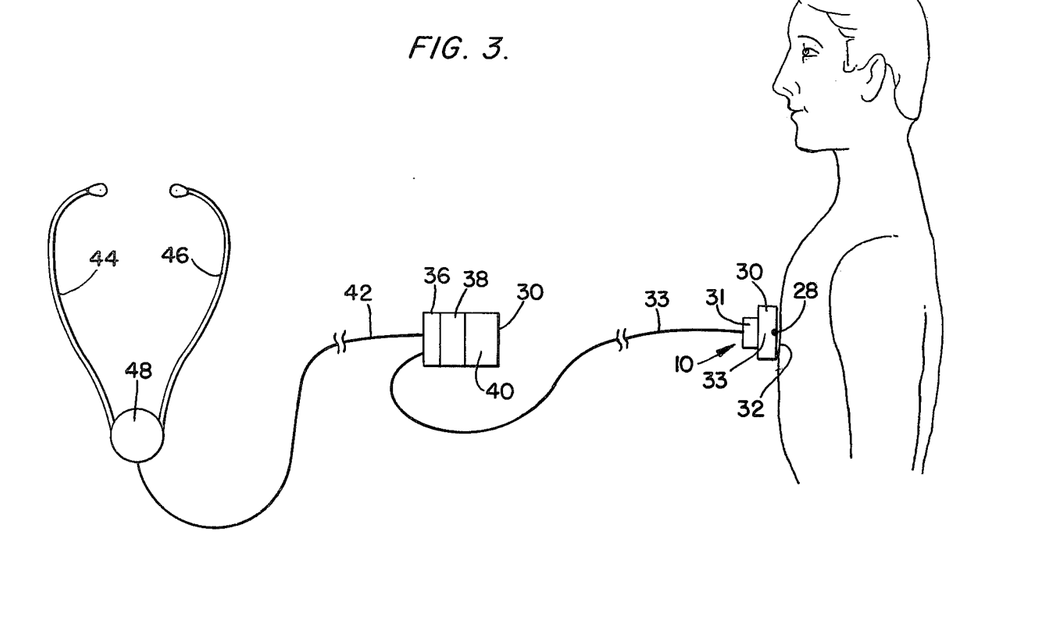
FIG. 3 is a diagramatic view of a microwave diagnostic instrument in accordance with the present invention.

Referring to FIG. 3, there is illustrated a portable microwave diagnostic instrument constructed in accordance with the present invention. As should be apparent, the instrument is specifically designed to approximate the physical appearance of a stethoscope. To this end, microprobe 10 is housed in a T-shaped cylindrical casing 30 having a flat surface 32 adapted to be placed against the skin of the subject. Diaphragm 32 includes a central window shaped to correspond to the output end of waveguide 16 and is in flush engagement with the outer perimeter of the exit end of the dielectric waveguide. A shielded cable 33 provides the necessary electrical connections between microwave source diode 12 and detector diode 28 to a solid state miniaturized integrated circuit conveniently packaged in casing 30. The integrated circuit includes a power source 36, amplifier 38 and a voltage to frequency converter 40 which provides an audio output signal correlated to the biophysical activity of the subject which in the case of FIG. 3 is cardiac activity. The output of the voltage to frequency converter is coupled via cable 42 to a pair of ear tubes 44 and 46 extending from spring member 48. Spring member 48 enables the ear tubes to be spread apart for insertion into the ears in a conventional manner. The output of the circuit may be monophonic or split between the two ear tubes to provide a binaural response.

Figure 4:
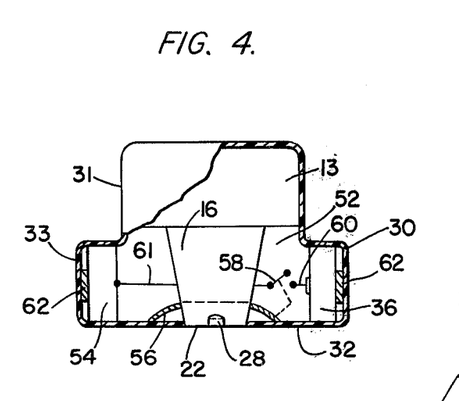
FIG. 4 is a partial diagramatic and enlarged view of the microwave diagnostic instrument of FIG. 3 showing a further embodiment of the "microprobe" in elevation with part of the housing removed for clarity.
Figure 5:
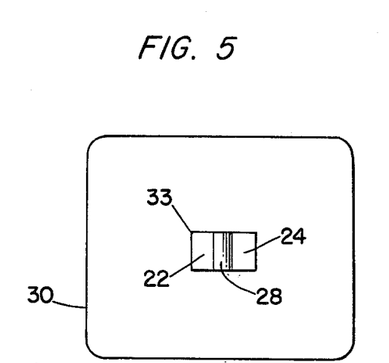
FIG. 5 is a bottom view of the "microprobe" of FIG. 4 looking into the waveguide exit ports.

As should be readily apparent, the packaging of the integrated circuit board enables the control components, together with the ear piece and microprobe element 10 to be slipped into and conveniently carried in a coat pocket, much the same as a stethoscope. Further miniaturization of the circuits onto semiconductor chips in accordance with conventional technology enables the power source 36, amplifier 40 and voltage to frequency converter 34 to be advantageously housed within the casing 30 for the microprobe element. To this end, as shown in FIGS. 4 and 5, Gunn diode 12 fits snugly within the upper section 31 of casing 30 which is of a reduced dimension compared to the base portion 33 of the casing. The area within the casing 30 and around waveguide 16 forms a cavity 52. At one end of cavity 52 is mounted a semiconductor chip 54 comprising the amplifier stages 38 and voltage to frequency converter 40. To the other side of cavity 52 is mounted power source or battery 36. Diaphragm 32 is coupled to a resilient spring element shown diagrammatically at 56 which operatively connects an on/off switch 58. Switch 58 is normally open until diaphragm 32 is pressed against the subject. Pressure on diaphragm 32 causes the spring element to flex and close switch 58 establishing electrical power connection between the Gunn diode and electrical circuits and the battery power source. To this end, switch 58 has one end connected by conductor 60 to the positive terminal of the power source 36 and its other end connected by suitable conductors 61 to chip 54 and diode 12. A common ground may be established through the use of a metal case or an internal metal band 62 within the case. Alternatively, the internal surface of the case may be provided with suitable conductive strips formed by thin layers deposited by conventional laminating processes.

Figures 6, 9:
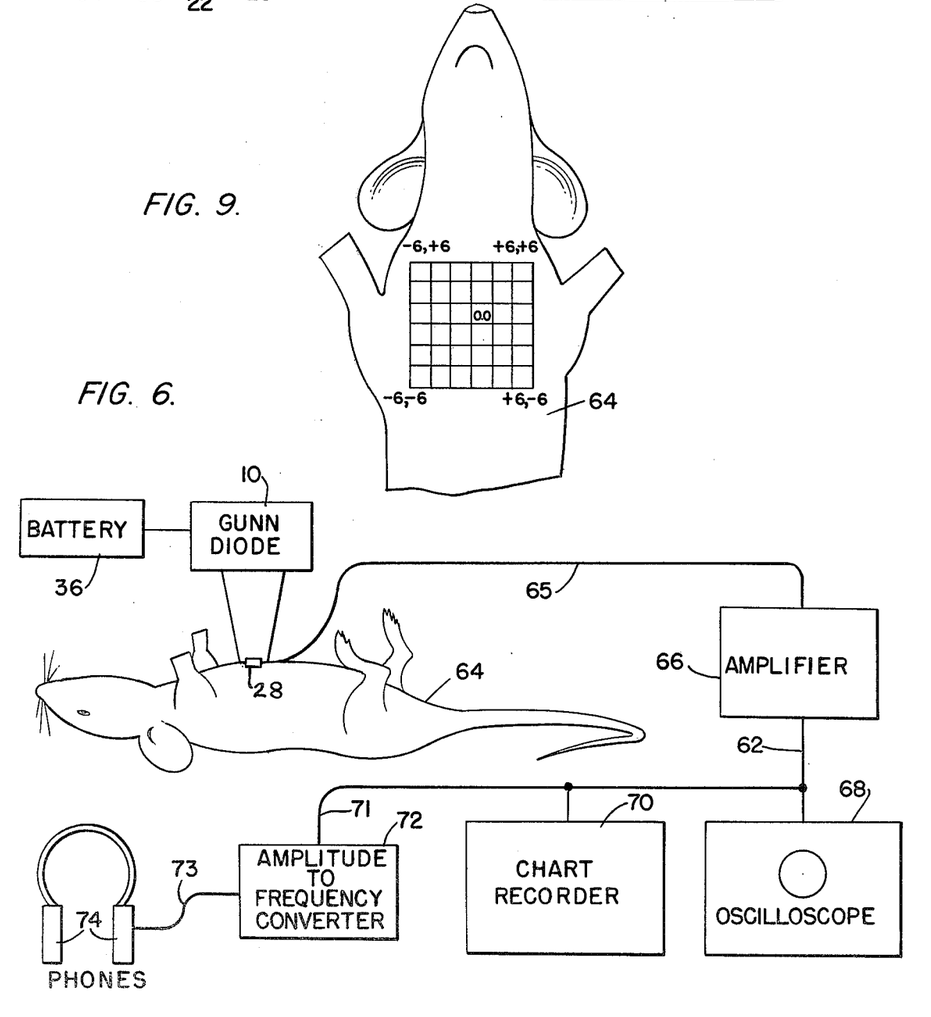
FIG. 6 illustrates a typical laboratory set up for the present invention for detecting heart activity in a mouse.
FIG. 9 shows a graphical representation of a target area scanned by the microprobe of the present invention.

Referring now to FIG. 6, there is shown a typical laboratory set up for monitoring cardiac activity of a mouse. Test results were obtained using an ICR mouse 64, female, adult weighing approximately 30 grams. The output detector 28 which may be a point contact Shottky diode is connected via shielded cable 65 to a AC amplifier stage 66 having a gain of $10^4$–$10^6$.

Amplifier stage 66 may include one or more conventional stages. Additionally, pre-amplifiers may be included. Conventional IC components may be utilized such as National Semiconductor quad op-amp 4 stage amplifier LM324N and National Semiconductor LM381AN pre-amplifier. The output of the amplifier 66 is coupled via conductor 67 to a oscilloscope 68 and a polygraph recorder 70 (Grass 7WC12PA) for making permanent recordings. An audio output is provided by connecting the output of amplifier 66 to an amplitude to frequency converter 72 which in turn has its output connected to head phones 74 via conductor 73.

Figure 7:
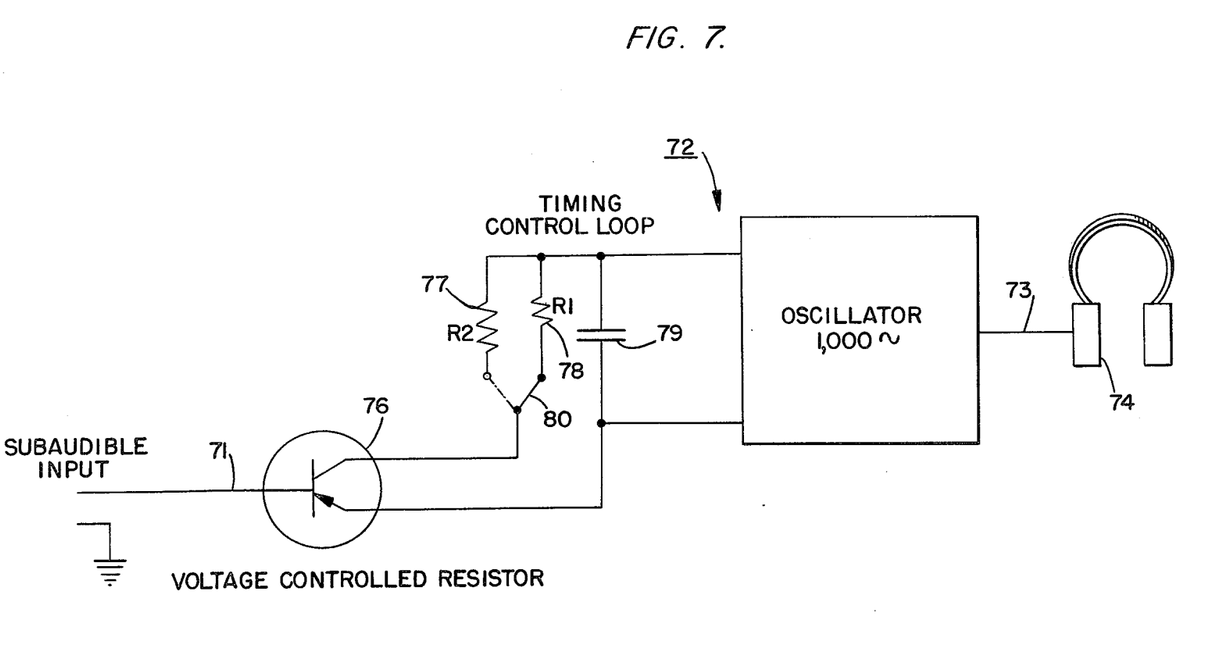
FIG. 7 is a combined schematic and diagramatic view of an amplitude to frequency converter in accordance with the present invention.

FIG. 7 illustrates a typical arrangement for achieving an audible response from backscattered radiation due to biophysical activity of a subject. The output of the Gunn diode is AC coupled to amplifier 66 to remove any DC components. The output of amplifier 66 provides a sub-audible signal which is applied via line 71 to base electrode input of transistor 76. Transistor 76 has its collector/emitter electrodes connected across an RC timing control loop comprising resistors 77 and 78 and capacitor 79. Resistors 77 and 78 are selectively connected into the circuit depending on the position of switch 80. Depending on which resistor is selected establishes whether breathing or lung sounds are filtered or incorporated into the output signal. Lung sounds appear as background noise and conventionally in a stethoscope the heartbeat is heard with the background breathing noise. In the present invention, by switching in a lower value resistance, the sounds due to slow voltage variations occasioned by breathing $$\left( \frac{dv}{dt} \text{ lung} < \frac{dv}{dt} \text{ heart} \right)$$

are effectively filtered out. The RC network sets the dc input level to the oscillator 82 which is a conventional 1000 cycle voltage controlled oscillator having its audio output connected to phones 74. Variations of the sub-audible input are thus translated into varying tone signals. Advantageously, a conventional squelch arrangement may be provided at the output of the oscillator to avoid low level noise in the phones.

The basic principle of operation consists of the fact that both the heart and the brain modulate an incoming continuous wave microwave signal; and that this modulation appears in the scattered beam. The scattered beam carries information imposed on it by the organ activity.

This modulated scattered wave is detected with a simple diode detector and converted into an identically modulated electric signal. The continuous component of the electric signal is removed by filtering while the sub-audible low frequency modulated signal components (up to approximately 100 Hz) are amplified, and monitored or displayed either on an oscillograph, or a chart recorder, or by conversion to an audio signal. Since these signals represent information imposed on the microwave radiation by the organ, they therefore reflect the operation of that organ.

This phenomenon provides a new technique for probing the physiologic activity, the anatomical structure, and the pathology of the various organs of living animals and man. At the present time, the mechanism for the modulation by the organ of the microwave radiation is not well understood. It was thought to reflect changes induced by mechanical activities of the various organs, but experiments tend to indicate the response may be due in part to electrical activity. Although the mechanism for modulation is not completely understood, nevertheless, with this new technique, it is exceedingly easy to obtain significant information regarding the activity of the heart. The modulation signals are rich and complicated, consisting of many peaks and valleys of different amplitudes and halfwidths. It is obvious that these signals contain a significantly larger quantity of information concerning heart activity than does the standard EKG. There is no apparent dead time in these signals. Because of the ease with which these signals can be obtained from a simple apparatus, they lend themselves well to utility in the medical field of cardiology. By scanning manipulations of the probe over the heart area, these signals may be used to present a visual image of various areas of the heart on an oscilloscope screen. Such an instrument would provide the cardiologist with a totally new capacity for examination of the heart function in animal and human patients for the detection of pathologic conditions.

The basic method was shown to work on mice. The mouse was anesthetized with an injection of sodium pentobarbital (1 cc, 40 mg/kg, injected subcutaneously under the skin of the back). The anesthetic was administered to make the animal tractable for the experiments, and is not necessary for the effect. The mouse is then turned on its back as shown in FIG. 6 and the microprobe positioned above the chest in contact with the skin. Skin contact enhances the strength of the signal and may either eliminate an additional source of extraneous reflected power from the air-skin interface, or provide a better impedance match for power transfer. The microwave power is turned on, and the electrical signal from the detector 28 is coupled to the solid state amplifier 66 of approximately 1000 gain. The input and output of the amplifier are both AC coupled. This removes the DC component.

Figure 8:
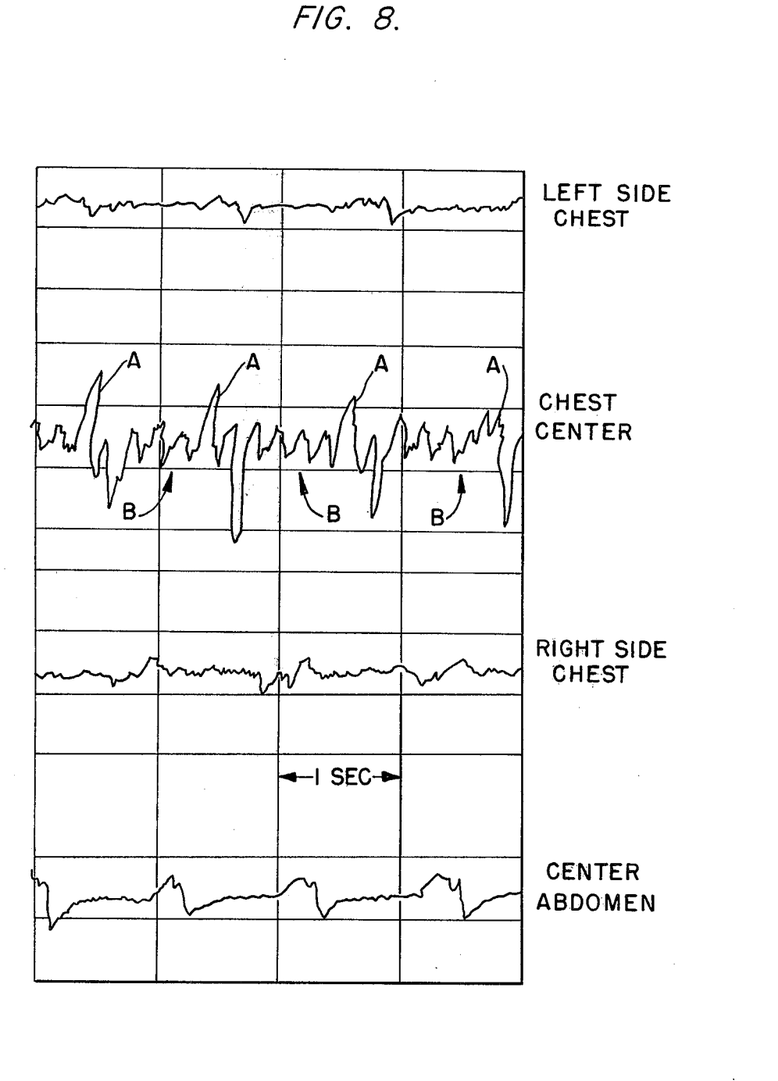
FIG. 8 illustrates modulated and microwave signals as recorded at various locations on the chest of a mouse using the microprobe of the present invention.

The band width of the amplifier is approximately 1000 Hz. The output of the amplifier was fed into a Grass Polygraph Recorder. In FIG. 8, there are presented a series of recordings taken on the Grass Polygraph Recorder used in a single channel mode. Each of the recordings is from a slightly different position on the chest. The chart speed is 25 mm/sec. The heart signals recorded can be obtained only from a region of roughly ½ cm², centered over the animal's heart. The signals consist of two different types. The first are the signals A appearing approximately once per second and are of high amplitude. These reflect the breathing mode of the animal. The pulses B that appear at approximately five per second are the heart beats of the animal. It can be seen that the modulated microwave signal for the heart beat consists of at least six, and possibly more, peaks and trough; that the shape of these modulated signals change with the position over the chest; and finally, that the signal strength is extremely high since the gain of the Grass Polygraph Recorder was set at 1 mv/cm. The signals change when the microprobe is moved away from the region of the heart, and, at a sufficient distance away, the microprobe can only pick up the signals due to the breathing mode, and the heart pulses have disappeared, as shown in the recording taken over the abdomen.

Figure 10:
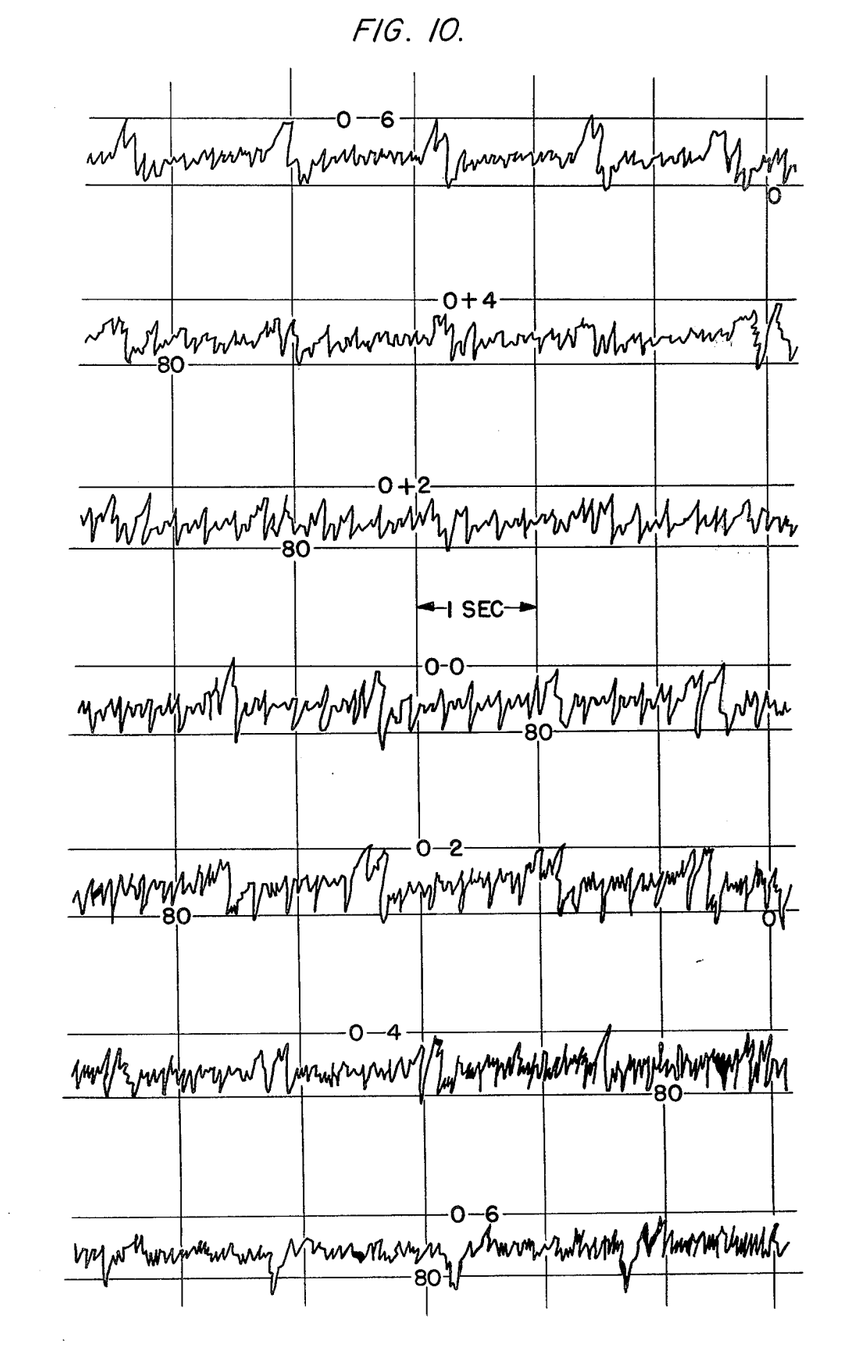
FIG. 10 shows the modulated microwave signal response taken along different points of the target area of FIG. 9.

Referring to FIG. 9, the chest of a mouse was graphed with a 6 mm square of 1 mm blocks, '0-0' refers to a position directly over the heart. The numbers, $+2$, $+4$, and $+6$, $-2$, $-4$, and $-6$, refer to successive 2 mm movements up and down, respectively, from the reference position 0,0. The graphs of FIG. 10 show the change in the nature of the signals as one scans a small portion of the animal's body around the mouse heart with a microprobe.

Figure 11:
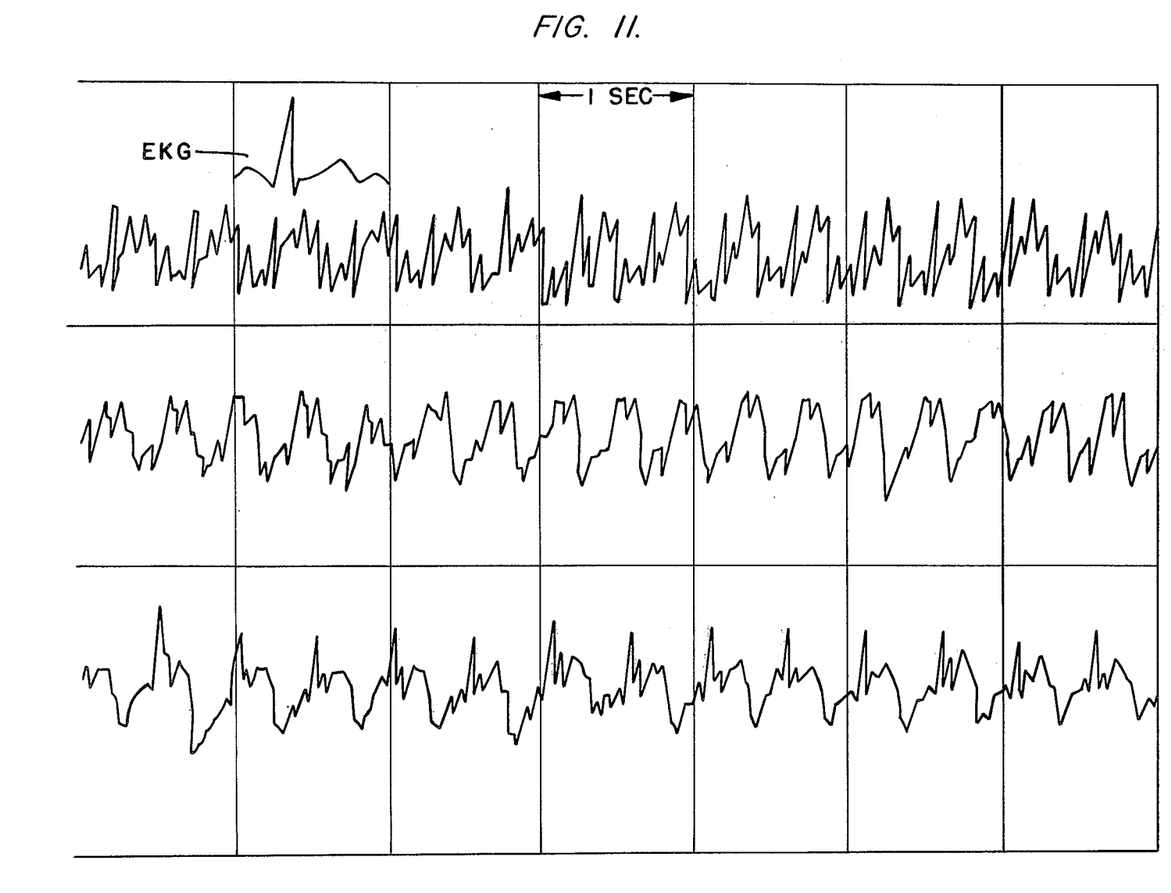
FIG. 11 shows a modulated, microwave signal response from a human heart taken at three different positions.

FIG. 11 shows a chart recording of modulated signals derived by the present invention from a human heart at three different positions. The variations suggest the localizability of the beam and the mapping capacity of the system. It is obvious that the human microwave cardiogram is far more complex than the standard electrocardiogram shown in the upper left hand corner of the recording. A significantly larger amount of information is embodied in the modulated microwave heart beat signal than is present in the EKG and the apparatus allows one to examine the physiologic activity of the heart in a living animal with minimal irritation and to obtain a rich supply of information that is presently beyond the capacity of the EKG and other known instruments.

A further development consists of a Stereophonic diagnostic instrument. By the use of two independent microprobes whose separation distance and angular orientations are selectively varied, there is provided a three-dimensional sound picture of the heart activity. The output of each microprobe is fed into one channel of a stereo amplifier, the output of which goes to one loudspeaker or channel of a stero amplifier, the output of which goes to one loudspeaker or headphone.

Another application is in microwave cardiography. As demonstrated above, the output of the diode can be fed directly to a chart recording for a permanent record. The resulting signal is a complex composed of a number of peaks of varying amplitudes and halfwidths. By comparing normal hearts with abnormal hearts, a determination of pathologic conditions of the heart by simple examination of the chart can be made. Also, the microprobe can be placed serially at different positions around the heart region of the chest to obtain additional information due to the different geometry; or the microprobe can be mechanically or electrically moved in a scanning pattern across the surface of the chest to provide additional information. Variations in the shape of the modulated signals with geometry can provide further information on the localization of abnormalities.

From any single microprobe in a given position over the chest cavity there is a time varying signal reflecting the microwave modulating activity of the heart. It is possible, by a number of known means, to convert this modulated signal into a visual display of the heart in actual real time movement.

For example, an array of microwave sources and detectors can be electrically scanned in a timed sequence and the outputs presented to the intensity control of a synchronously scanned oscilloscope beam. The time for one complete scan must be short compared to the movement time of the heart. This, then, provides a rough two-dimensional picture in time of the heart movement. An alternative embodiment would be to have the microprobe movement rapidly scanning the chest cavity in synchrony with the oscilloscope beam. The microwave beam may also be converted from a continuous wave to a pulsed beam, with the pulse frequency sufficiently high so that the scanning beam time for one frame would give a good resolution. The parameters are not too dissimilar to a vidicon television system.

As hereinbefore noted, modulation due to heart activity has generally been thought to be the results of mechanical muscle movement. However, experiments in connection with microwaves scattered from the heads and spinal cords, contain modulations in amplitude which reflect on going biological activity in these organs and which suggest the response is due to neural activity and interaction on the input beam.

The animals used in the detection of brain activity are the ICR mouse, female, adult, weighing approximately 30 grams, and the Dutch belted rabbit, female, adult, weighing approximately 1 kilogram. The animals were anesthetized with sodium pentobarbital to put them in the dormant state. The animals were then mounted in a stereotaxic holder made of wood and glass to minimize disturbance of the microwaves. These heads are rigidly restrained. The microprobe is placed on the dorsal surface of the head of the anesthetized animal. The probe need not make direct contact with the skin for signals to be obtained. In some cases the animal's fur was shaved, and, in one case, the skin of the surface of the head was resected to expose the skull. In this latter case the same signals were obtained, thus removing the possibility that skin or muscle movements are the source of the signals.

The modulated signals consist of a variety of types, differing in frequencies, amplitudes and wave forms. The dominant form of activity sensed by the microprobe is the lowest frequency range, between 0.5 and 2 hertz. These signals are rhythmic pulsations which are closely associated with the animal's respiration. These signals may be monophasic, or, as is more usual, biphasic. These types of signals are called "breathing modes". In some cases they appear to be sharp, with a full width at half maximum, of about 0.1 seconds; in other cases the width can be 3 to 4 times larger. A second type of signal found in the rabbit, related to these "breathing mode" spikes are those resembling alpha wave spindles. These are at a frequency of 8 hertz, while interspindle spikes occur at a frequency of about 16 hertz. Similar signals in the mouse do not appear to be related to the "breathing modes". The high frequency cutoff of the polygraph eliminated possible higher frequency components.

Figure 12:
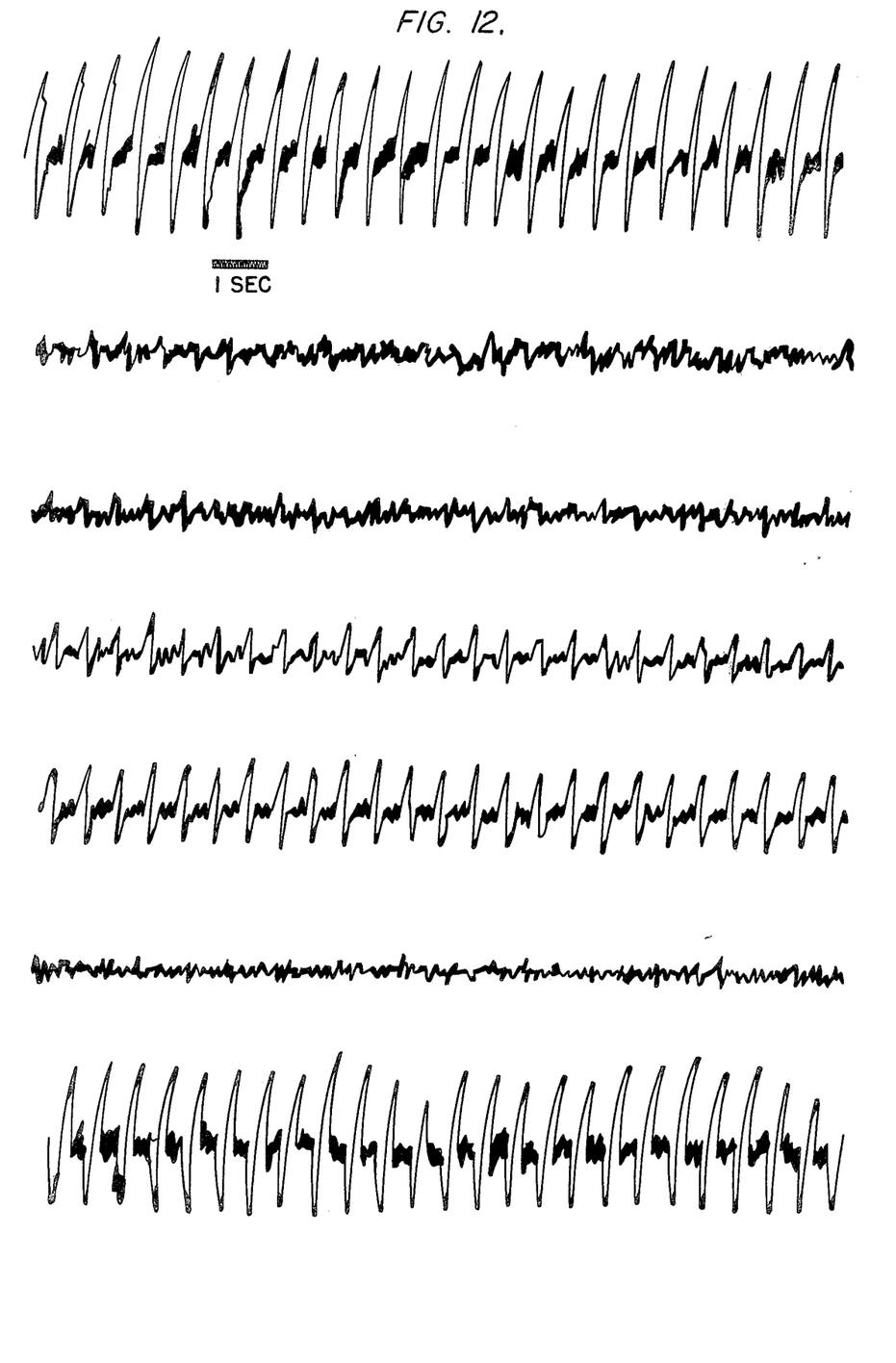
FIG. 12 shows modulated, microwave signals developed from matched diodes arranged in a semi-circular pattern on the dorsal surface of the head of an animal.

With either a dead animal, or one in a deeply anesthetized state (though still breathing) no signals are detected. As the anesthetic wears off (though the animals are still torpid) the signals emerge from the background noise thus monitoring the depth of anesthesia. These signals are shown in FIG. 12 as recorded by an array of 7 different, but roughly matched, diodes arranged in a semicircle above the head, from left to right. The microwave beam entered frontally at a 90° angle to the array. These, and other data, illustrate that the "breathing mode" is not distributed uniformly across the head. The spatial distribution varies smoothly as a function of position of the diode array. Bilateral asymmetry is often observed. The "breathing mode" is variable in time at a given position, i.e. particular positions alternately pulsated and then became silent for a period of many minutes. The wave form also can appear in a mirror image of itself in various places on the cranium at different times.

Figure 13:
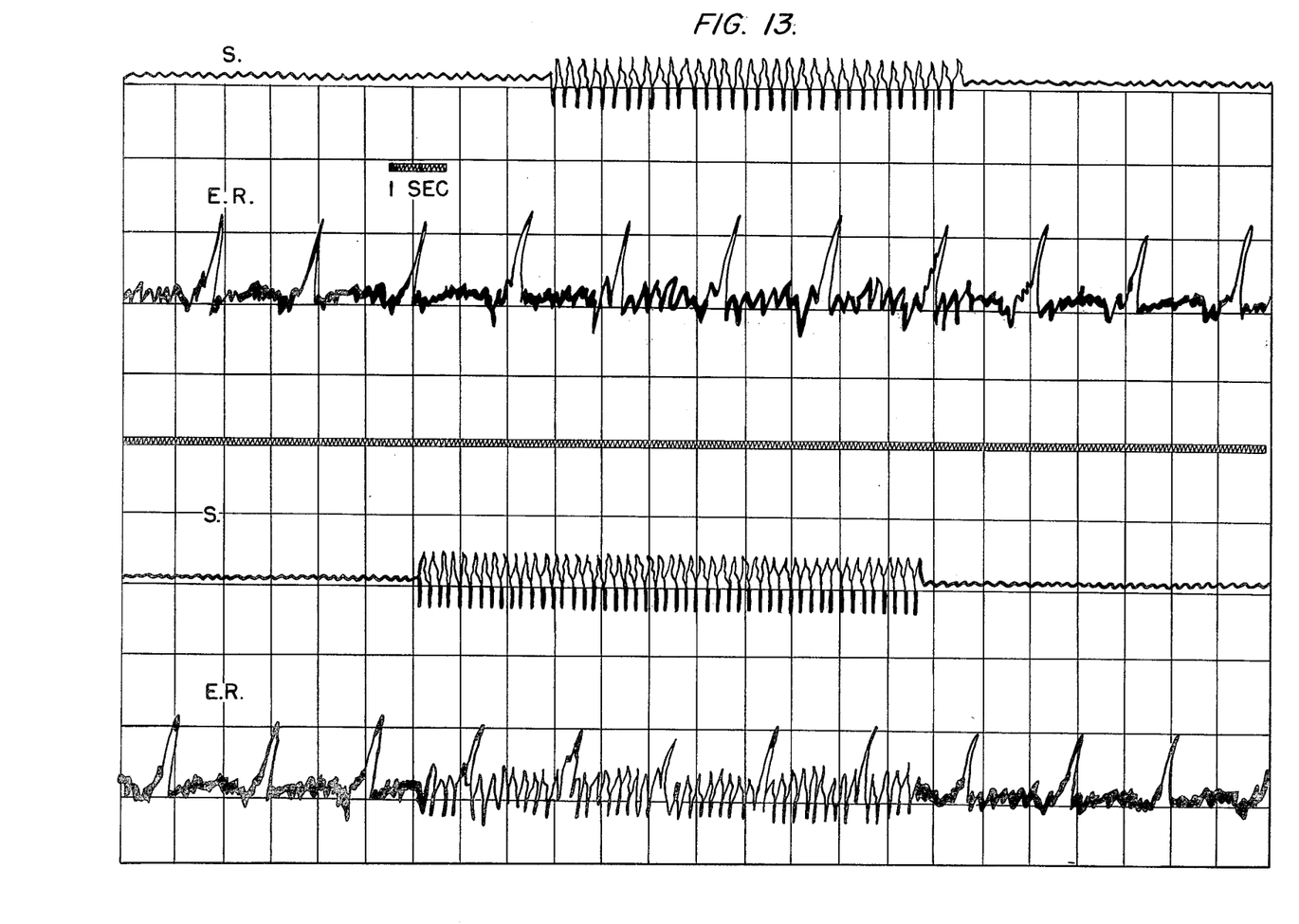
FIG. 13 shows recordings obtained from the occipital regions of a head of an animal when stimulated with a light source.

The confirmation that these microwave signals reflect electrical activity of the brain is the appearance of evoked responses. Such signals have appeared in both the mouse and the rabbit using a variable frequency light source. A light emitting diode was chosen whose light was in the yellow spectral region. The frequency was controlled by applying a sinusoidal voltage to it from an Ando ULO-5 oscillator. To avoid electrical interference with the microprobe, the light from the diode was conducted via a 30 cm. glass rod to the eye of the dark adapted animal. The microwave semiconducting diode detector was shown to be insensitive to visible light, and, in any case, a black cloth covered the head of the animal, preventing the light from reaching the diode. On a number of occasions, a change in the microwave signals when the stimulus was applied has been observed. A recording, clearly showing an entrainment of the microprobe signals with the light signals, is shown in FIG. 13. These recordings were obtained from the occipital regions of the head.

Figure 14:
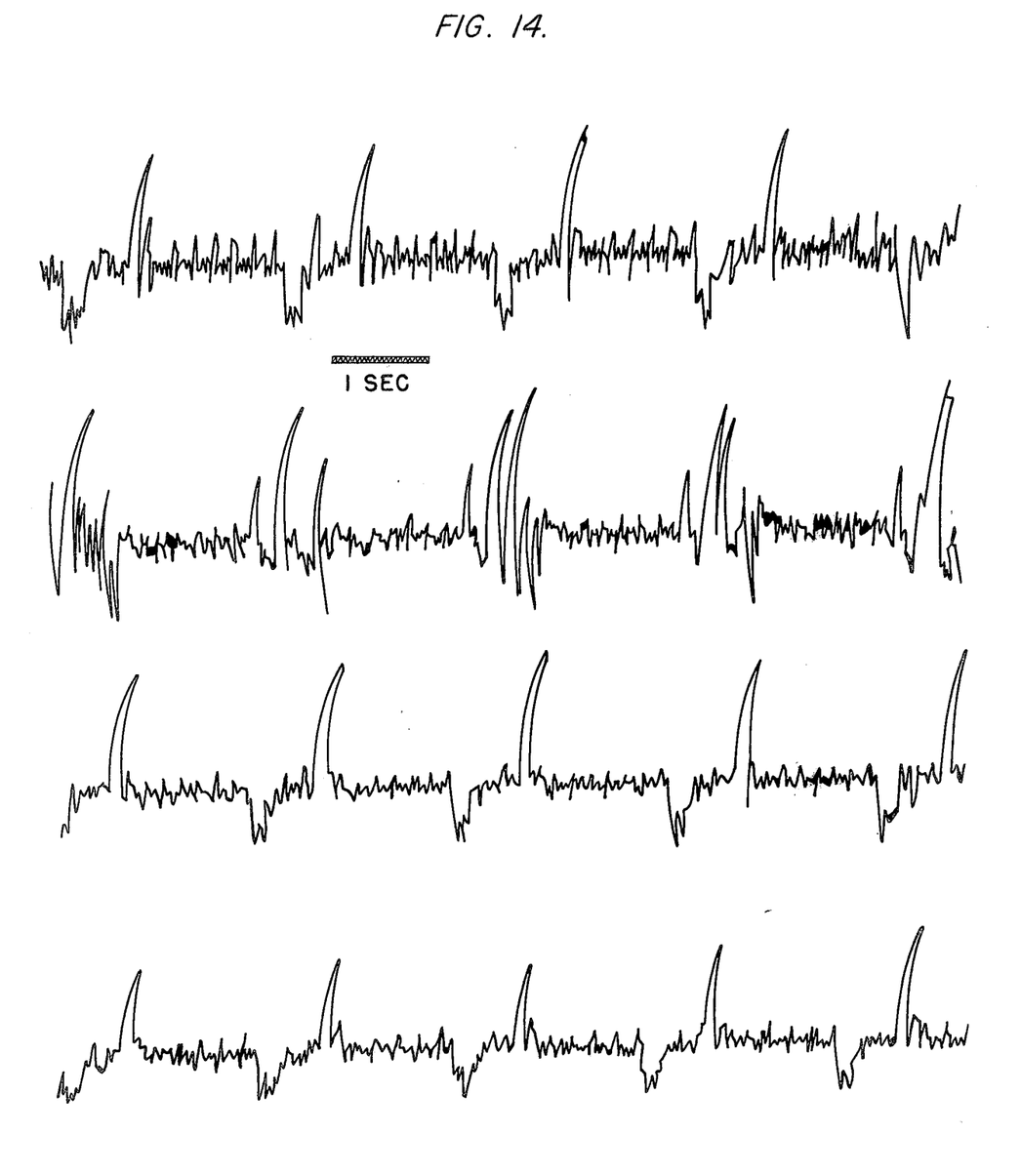
FIG. 14 shows recordings obtained from the spinal cord of an animal.

The microprobe of the invention has also been used to probe the spinal cord of both the mouse and the rabbit and the resultant modulated signals obtained are illustrated in FIG. 14. Movement of the microprobe a few millimeters away from the spine in either direction causes a loss of these signals. These signals contain the "breathing mode" pattern with a superimposed spike frequency at 6 hertz, plus smaller amplitude, but higher frequency spikes at 16 hertz. For purposes of comparison, it is noted that the heart beat rate as determined by the probe over the animal's chest was 4-5 hertz for the mouse and 3-4 hertz for the rabbit. Thus, neither the brain nor the spinal cord signals can easily be attributed to the heart movement, or to coordinated blood pressure waves.

The simplest assumption to make is to attribute the signals we have reported here to purely mechanical movements, but it has become difficult to sustain this argument. The fact that the signal strength is a function of the depth of anesthesia, and does not appear in a deeply anesthetized animal which is still breathing, cannot easily be reconciled with purely mechanical movements. The plasticity of the signals, both with position and time, the changes in wave form, and the evident asymmetry across the head, further increase our doubts. The appearance of evoked response activity suggests more than a purely mechanical source for these signals. We, therefore, believe that it is at least possible that some, if not all, of these microprobe signals reflect, either directly or indirectly, underlying electrical activity of the brain and spinal cord.

We claim:

1. A portable microprobe for non-invasive monitoring of biophysical activity associated with cardiac and neural activity of a life system comprising means for generating microwave radiation, a dielectric waveguide having a reducing taper coupled at its larger end to said microwave radiation generating means for concentrating and directing a localized beam of radiation through its smaller end into a localized area of the life system of interest and means at said smaller end for detecting modulated backscattered radiation from the life system of interest.

2. A microprobe as set forth in claim 1, wherein said waveguide is shielded along its outer surface with a layer of metal.

3. A microprobe as set forth in claim 2, wherein said metal is selected from the group of gold, silver, copper and aluminum.

4. A microprobe as set forth in claim 1, wherein said dielectric waveguide has a groove at its smaller end and said means for detecting backscattered radiation is disposed in said groove.

5. A microprobe as set forth in claim 4, wherein said groove is lined with a metallic shield.

6. A microprobe as set forth in claim 5, wherein said shield is selected from the group consisting of gold, silver, copper and aluminum.

7. A microprobe as set forth in claims 1, 2, 3, 4, 5 or 6, wherein said dielectric is a plastic transparent to microwaves.

8. A microprobe as set forth in claim 7, wherein said plastic has incorporated therein a filler for modifying the dielectric constant of the plastic.

9. A microprobe as set forth in claim 8, wherein the filler is titanium dioxide.

10. A microprobe as set forth in claim 1, further including means connected to said detecting means and responsive to a signal therefrom for providing an output to enable monitoring of said biophysical phenomena.

11. A microprobe as set forth in claim 10, wherein said connected means includes a chart recorder for providing a permanent record of said output.

12. A microprobe as set forth in claim 10, wherein said connected means includes a audio oscillator for providing an audible output corresponding to the monitored biophysical activity.

13. A microprobe as set forth in claim 1, wherein the waveguide tapers to a cross sectional dimension of approximately 1 square centimeter at its smaller end.

14. A microwave diagnostic instrument for monitoring biophysical activity associated with cardiac and neural activity of a life system comprising a casing, a source of low power microwaves within said casing, means within said casing and coupled to said source for concentrating and directing the radiation into a localized beam of radiation from said source through an exit opening provided in said casing, detecting means disposed at said opening for detecting modulated backscattered radiation from the life system of interest and means connected to said detecting means for developing a signal modulated in accordance with the detected modulated backscattered radiation.

15. A microwave diagnostic instrument as set forth in claim 14, including means for shielding said detecting means from said localized beam of radiation.

16. A microwave diagnostic instrument as set forth in claim 14, wherein said detecting means is disposed in the path of said beam of radiation and further including means for shielding the detector from the beam.

17. A microprobe as set forth in claim 14, wherein said means within said casing comprises a waveguide shielded along its outer surface with a layer of metal selected from the group of gold, silver, copper and aluminum, said waveguide having a reducing taper extending from said source to the exit opening.

18. A microprobe as set forth in claim 17, wherein said waveguide is a dielectric waveguide including a plastic transparent to microwaves, said plastic having incorporated therein a filler of titanium dioxide for modifying the dielectric constant of the plastic.

19. A microprobe as set forth in claim 17, wherein the waveguide tapers to a cross sectional dimension of approximately 1 square centimeter at the exit opening.

20. A microprobe as set forth in claim 18, wherein said waveguide includes a groove cut at the exit opening and said means for detecting backscattered radiation is disposed in said groove.

21. A microprobe as set forth in claim 20, wherein said groove is lined with a metallic shield selected from the group consisting of gold, silver, copper and aluminum.

22. A microprobe as set forth in claim 18, further including means connected to said detecting means and responsive to a signal therefrom for providing an output to enable monitoring of said biophysical phenomena.

23. A microprobe as set forth in claim 22, wherein said means connected to said detecting means includes a chart recorder for providing a permanent record of said output.

24. A microprobe as set forth in claim 23, wherein said connected means includes an audio oscillator for providing an audible output corresponding to the monitored biophysical activity.

25. A microwave diagnostic instrument as set forth in claim 1 or 18, wherein said beam is concentrated in a pencil shaped beam having a cross-sectional diameter of approximately 1 cm. square.

26. A portable microprobe adapted to emit microwave radiation at a power level of less than 10 milliwatts for non-invasive monitoring of biophysical activity associated with cardiac and neural activity of a life system, comprising a casing, a microwave source disposed within said casing for feeding radiation into one end of an insulated dielectric waveguide, said waveguide terminating in a free end, a semiconductor diode disposed at said free end and being shielded by a metal shield from the incident beam of radiation fed from said microwave source, said wave guide having a reducing taper in the direction of the free end so as to concentrate and deliver a pencil shaped beam of radiation into the life system, said diode being operatively connected to a receiver system so as to receive back-scattered radiation from the life system, said back-scattered radiation being modulated and detected by said diode to develop a signal indicative of the activity being monitored and means responsive to said signal for providing an output indicative of the on-going activity.

27. A microprobe as set forth in claim 26, wherein said receiver system is housed in a self-contained package external of the casing and connected to receive the output of the diode, said receiver system having an output connected through a flexible attachment to an ear piece which enables continuous monitoring of the audio response.

28. A portable microprobe as set forth in claim 26, wherein said microwave source is a diode.

* * * * *

UNITED STATES PATENT AND TRADEMARK OFFICE
CERTIFICATE OF CORRECTION

PATENT NO. : 4,344,440
DATED : August 17, 1982
INVENTOR(S) : Trygve Aaby et al

It is certified that error appears in the above—identified patent and that said Letters Patent are hereby corrected as shown below:

Claim 20, column 12, line 13, change "18" to --14--.

Claim 22, column 12, line 22, change "18" to --14--.

Claim 25, column 12, line 35, change "18" to --14--.

Signed and Sealed this

Ninth Day of November 1982

[SEAL]

Attest:

Attesting Officer

GERALD J. MOSSINGHOFF

Commissioner of Patents and Trademarks